(12) United States Patent
Huang (10) Patent No.: US 6,596,774 B1
(45) Date of Patent: Jul. 22, 2003

(54) SYNTHESIS, LIPID PEROXIDATION AND CYTOTOXIC EVALUATION OF 10-SUBSTITUTED 1,5-DICHLORO-9(10H)-ANTHRACENONE DERIVATIVES

(76) Inventor: Hsu-Shan Huang, 5F, No. 134, Wern-Hwa 3 Road, Peitou 112, Taipei (TW)

( * ) Notice: Subject to any disclaimer, the term of this patent is extended or adjusted under 35 U.S.C. 154(b) by 0 days.

(21) Appl. No.: 09/965,774

(22) Filed: Sep. 27, 2001

(51) Int. Cl.[7] .......................... A61K 31/12; C07C 50/16
(52) U.S. Cl. ...................... 514/676; 514/680; 552/289; 552/290
(58) Field of Search ................ 552/290, 289; 514/676, 680

(56) References Cited

PUBLICATIONS

Beilstein Record 3388717; Feb. 15, 1990.*
Beilstein Record 3414294; Feb. 15, 1990.*
Beilstein Record 3458641; Feb. 15, 1990.*
Haung et al., Studies on anthracenes, Chemical & Pharmaceutical Bulletin, 2001, 49(10), 1288–91.*
Cook et al, Recl. Trav. Chim. Pays–Bas, 44, 1925, 897.*
Barnett et al, Chem.Ber., 62, 1929.*
Preparation of Anthraquinones From 10–Hydroxy–9Anthracenecarbonitriles Obtained From a Novel Aryne Annulation Reaction, Bhawal, et al, J. Org. Chem, vol. 56, No. 8, 1991, pp. 2846–2849.
Studies Related to the Conversion of 9,10–Anthraquinones to Anthracenes, Criswell, et al, J. Org. Chem, vol. 39, No. 6, 1974, pp. 770–774.
Synthesis and Antitumor Evaluation of 2,5–Disubstituted––Indazolo[4,3–GH]Isoqunolin–6(2H)–Ones (9–Aza–Anthrapyrazoles), Krapcho, et al, J. Med. Chem. 1998 41, 5429–5444.
Antipsoriatic and Proinflammatory Action of Anthralin—Implication for the Role of Oxygen Radicals, Klaus Muller, Biochemical Pharmacology, vol. 53, pp. 1215–1221, 1997.
Antipsoriatic Anthrones With Modulated Redox Properties. 3. 10–Thio–Substituted 1,8–Dihydroxy–9(10H)–Anthracenones as Inhibitors or Keratinocyte Growth, 5–Lipoxygenase, and the Formation of 12(2)–Hete in Mouse Epidermis, Muller, et al, Journal of Medicinal Chemistry, vol. 39, No. 16, pp. 3132–3138.

Syntheses of Anthracenones. 1. Sodium Dithionite Reduction of Peri–Substituted Anthracenediones, J. Org. Chem, 1996, 61, 2853–2856.
Conversion of Alkoxy–9,10–Anthraquinones to Alkoxyanthracenes, Shyamasundar, et al, J. Org. Chem, 1981, 46, 809–811.
Lithium Aluminum Hydride Reduction of Peri–Alkoxy–9, 10–Anthraquinones, Shyamasudar, et al, J. Org. Chem, 1981, 46, 1552–1557.
N–Allylsecoboldine as a Novel Antioxidant Against Peroxidative Damage, Teng, et al, European Journal of Pharmacology 303, 1996, 129–139.
Studies on Anthracenes. 3. Synthesis, Lipid Peroxidation and Cytotoxic Evaluation of 10–Substituted 1,5–Dichloro–9(10H)–Anthroacenone Derivatives, Huang, et al, Chem. Pharm. Bull. 49, No. 10, 2001 Pharmaceutical Society of Japan.
Studies on Anthracenes. 1. Human Telemerase Inhibition and Lipid Peroxidation of 9–Acyloxy 1,5–Dichloroanthracene Derivatives, Huang, et al, Chem. Pharm. Bull. 49(8) 969–973, 2001 Pharmaceutical Society of Japan.

* cited by examiner

*Primary Examiner*—Alton N. Pryor
(74) *Attorney, Agent, or Firm*—Stephen M. Nipper; Robert L. Shaver; Frank J. Dykas (57) ABSTRACT

The present invention is the synthesis of a series of 1,5-dichloro-9(10H)-anthracenones bearing O-linked and N-linked substituents in the 10-position. These compounds were evaluated for their ability to inhibit the growth of the human oral epidermoid carcinoma cells (KB cell line), human cervical carcinoma cells of ME 180 (GBM 8401) and Chinese hamster ovary cells (CHO), respectively. In addition, redox property of the compounds for inhibition of lipid peroxidation in model membranes was determined.

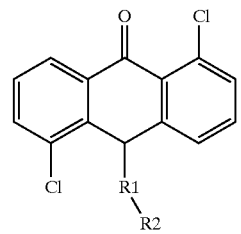

6 Claims, 2 Drawing Sheets

Figure 1

Figure 2 (Scheme 1)

(a): $Br_2$, $CS_2$; (b): $CaCO_3$, THF, $N_2$, R-OH or R-$NH_2$. R is defined in Table 1.

SYNTHESIS, LIPID PEROXIDATION AND CYTOTOXIC EVALUATION OF 10-SUBSTITUTED 1,5-DICHLORO-9(10H)-ANTHRACENONE DERIVATIVES

BACKGROUND OF THE INVENTION

Field of the invention. The synthesis of a series of 1,5-dichloro-9(10H)-anthracenones bearing O-linked and N-linked substituents in the 10-position are described. These compounds were evaluated for their ability to inhibit the growth of the tumor, and lipid peroxidation in model membranes.

Description of the prior art. Anthracenone derivatives display potent and selective antitumor activity, but their mechanism of action is not clearly established yet. Despite structural similarities between the substitutents anthracenone nucleus and molecules possessing known antitumor activity, antiproliferative, antipsoriatic, antiinflammatory, or antioxidant activity, these agents form a distinct mechanictic class. Perry P. J., et al., J. Med. Chem., vol. 41, pp. 3253–3260, 4873–4884 (1998); Perry P. J., et al., J. Med. Chem., vol. 42, pp. 2679–2684 (1999). Anthracene and anthracenone derivatives have been the subject of extensive research mainly due to their well-recognized biological importance and the significant biological applications. Although potential drug targets only present in cancerous cells have surfaced, the design of a drug which is selectively toxic to a tumor and not to the host organism is still very difficult have reported by Krapcho A. P., et al., J. Med. Chem., vol. 41, pp. 5429–5444 (1998).

We have previously shown that 9-acyloxy 1,5-dichloroanthracenes at WO 0061536 and 9-acyloxy 1,8-dichloroanthracenes on Chem. Pharm. Bull., vol. 49(8), pp. 969–973(2001). In the previous papers, we described the synthesis, biological evaluation and structure-activity relationships for 9-acyloxy derivatives. In order to provide further insight into anthracene and anthracenone pharmacophore, the involvement of free radicals and antiproliferative activity, we examined the effects of introducing electron-donating 10-oxy and 10-N substituents to see where replacement of the electron-withdrawing carbonyl of the earlier series can provide analogs with both potent antioxidant and antiproliferative activities. Despite the extensive and long-standing therapeutic utilization of anthracenones, their mechanism of action is still uncertain. A large body of evidence is consistent with a fundamental role of oxygen radicals in the induction of skin inflammation by anthracenes of Müller K., Biochem. Pharmacol., vol. 53, pp. 1215–1221 (1997).

The mode of action of anthracenones leads to the conclusion that no single mechanism is predominantly operative and oxygen radicals play a crucial role in the proinflammatory action. As noted above, cancer is typically characterized by hyperproliferative component. There is thus a continuing need for effective compounds that address these aspects of cancer disease. To gain a wider understanding of the involvement of radicals in the action of anthracenone-derived agents, several related compounds bearing selected characteristic functional groups were designed. The approach was to develop structure-activity relationships (SARs) of 9(10H)-anthracenone analogs with redox-active centers attached to the anthraquinone skeleton through spacer side chains at position 10, together with substituents with DNA-binding affinity. This paper describes the design and synthesis of anthracenones that incorporate in their structure a potential antioxidant component and the results of relevant biologic studies.

SUMMARY OF THE INVENTION

The present invention is described the novel 1,5-dichloro-9(10H)-anthracenones bearing O-linked and N-linked substituents compounds and analogs thereof having therapeutic utility with respect to tumor conditions or antioxidant activity. In particular, many of the improved anthracenone compounds provided for according to the practice of the invention are effective at low concentrations for treatment of patients suffering from tumor conditions or antioxidant activity.

Figure 1:
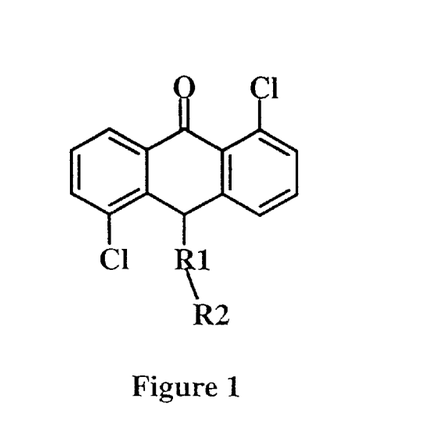
FIG. 1 shows the structural of 10-substituted 1,5-dichloro-9(10H)-anthracenones of formula 3.
Figure 2:
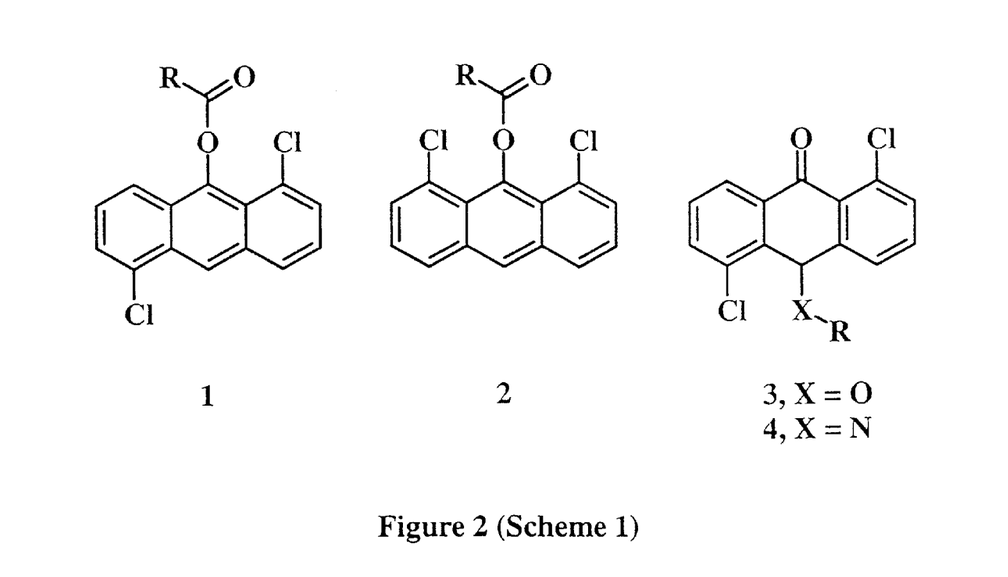
FIG. 2 shows the structural of 9-acyloxy 1,5-dichloroanthracenes and 9-acyloxy 1,8-dichloroanthracene.

Accordingly, in one embodiment of the invention, there is provided an anthracene compound according to formula 3 as defined below and shown in FIG. 1, said compound containing substituent $R_1$, wherein $R_1$ represents oxygen, nitrogen. The substituent $R_2$, wherein $R_2$ represents a branched or straight chain alkyl group having from 1 to 4 carbon atoms, said alkyl group being substituted with at least one substituent selected from the group consisting of a carboxyl, hydrogen, substituted phenyl, benzyl and substituted benzyl groups or a substituted phenyl group.

Still other objects and advantages of the present invention will become readily apparent to those skilled in this art from the following detailed description wherein I have shown and described only the preferred embodiment of the invention, simply by way of illustration of the best mode contemplated by carrying out my invention. As will be realized, the invention is capable of modification in various obvious respects all without departing from the invention. Accordingly, the drawings and description of the preferred embodiment are to be regarded as illustrative in nature, and not as restrictive.

DETAILED DESCRIPTION OF THE INVENTION

While the invention is susceptible of various modifications and alternative constructions, certain illustrated embodiments thereof have been shown in the drawings and will be described below in detail. It should be understood, however, that there is no intention to limit the invention to the specific form disclosed, but, on the contrary, the invention is to cover all modifications, alternative constructions, and equivalents falling within the spirit and scope of the invention as defined in the claims.

The 1,5-dichloro-9(10H)-anthracenones bearing O-linked and N-linked substituents that presents as formula 3 as defined below, said compound containing substituent $R_1$, wherein $R_1$ represents oxygen, nitrogen. The substituent $R_2$, wherein $R_2$ represents a branched or straight chain alkyl group having from 1 to 4 carbon atoms, said alkyl group being substituted with at least one substituent selected from the group consisting of a carboxyl, hydrogen, substituted phenyl, benzyl and substituted benzyl groups or a substituted phenyl group.

formula 3

Introduction of side chains onto the anthracenone nucleus is usually accomplished by a stepwise procedure via the anthracenedione because of the chemical instability of many anthracenones. Therefore, reduction of 1,5-dichloroanthraquinone and bromination are required in the synthesis of C-10-substituted anthracenones. Although several excellent methods are available for the reduction of anthracenediones, many reducing systems do not lead directly to the anthracene stage. Criswell T. R., et al., J. Org. Chem., vol. 39, p. 770 (1974); Shyamasundar N., et al., J. Org. Chem., vol. 46, pp. 809–811, 1552–1557 (1981).

Figure 3:
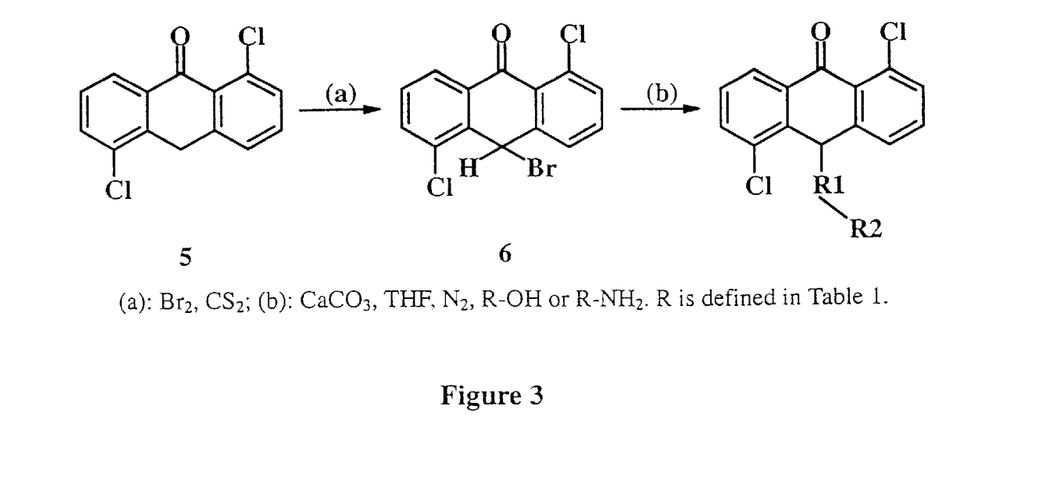
FIG. 3 (Scheme 1) shows the synthesis step of the target 10-substituted 1,5-dichloro-9(10H)-anthracenones of formula 3.
Figure 4:
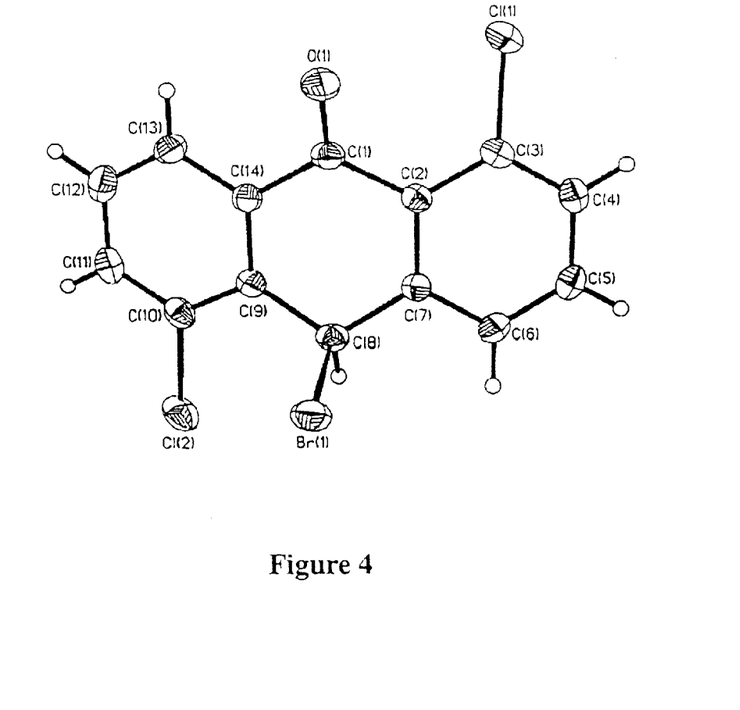
FIG. 4 shows X-ray crystal structure of compounds 6.

The traditionally employed methods that lead preferentially to the anthracenones include stannous chloride in acetic acid/hydrochloric acid there were reported by Müller K., et al., J. Med. Chem., vol. 39, pp. 3132–3138 (1996); Prinz H., et al., J. Org. Chem., vol. 61, pp. 2853–2856 (1996). Thus, treatment of compound 5 with bromine provide 10-Bromo 1,5-dichloro-9(10H)-anthracenone (6) which have prepared by Müller K., et al., J. Med. Chem., vol. 39, pp. 3132–3138 (1996). Bromination of anthracenone take place at the 10-position. The structure of compound (6) was confirmed by X-ray analysis. The ORTEP plot of compound (6) is shown in FIG. 4; the bond lengths and bond angles for this structure are listed in experimental. A series of 10-substituted 1,8-dichloro-9(10H)-anthracenones were synthesized from compound (6) by nucleophilic substitution at C-10 with 1.5–2.0 equivalents of appropriate amines or alcohols in the presence of catalytic amounts of $CaCO_3$, which strongly reduced the reaction time as compared to the noncatalyzed reaction. The 10-oxy-substituted and 10-N-substituted 1,8-dichloro-9(10H)-anthracenones were synthesized readily according to scheme 1 (FIG. 3).

The structures of these compounds were established on the basis of spectroscopic analysis. The $^1$H-NMR spectra of compound (6) show a singlet at $\delta 6.62$ for the C-10 of H, doublet at $\delta 8.11$ for the proton at position 8 and dd at $\delta 7.65$ for the proton at position 6. Of particular importance of these series compounds are the one proton chemical shifts at position 10 between $\delta 5.31$ and 6.08, which are difference from the range of the compound 5 possessing two 10-H protons at $\delta 4.32$, and the IR stretching frequency which is indicative of C=O stretch. Furthermore, the $^{13}$C-NMR spectra of these compounds show the usual carbonyl absorbance signal in the $\delta 180$–190 region. Bhawal B. M., et al., J. Org. Chem., vol. 56, pp. 2846–2849 (1991).

In the previous papers, we described the synthesis and some biological evaluation for 9-acyloxy 1,5-dichloroanthracenes and 9-acyloxy 1,8-dichloroanthracenes, respectively. In general, results from these assays did not show a reasonable correlation.

We evaluated the ability of the compounds to inhibit the growth of human oral epidermoid carcinoma cells (KB cell line), human cervical carcinoma cells of ME 180 (GBM8401) and Chinese hamster ovary (CHO) cells as normal cells, and lipid peroxidation in model membranes, respectively. The compounds were tested for cytotoxic activity assay as demonstrated by reduction in cell number over time as compared to control plates. The results are shown in Table 1.

Our study on the cytotoxicity evaluation of 10-substituted 1,8-dichloro-9(10H)-anthracenone derivatives have revealed that compounds 4a, 4c and 4d exhibited high cytotoxicity and significant activity on GBM in vitro assay; compounds 3c, 4b and 4c exhibited high cytotoxicity and significant activity on KB in vitro assay. Only compounds 3a, 4c and 4d were more toxic in CHO than mitoxantrone. Although there were no obvious requirements for potent antiproliferative activity, the inhibitory effects of these compounds appear to be due to some selective cell lines rather than nonspecific redox properties. In addition to the redox properties, other factors such as an appropriate geometry of the molecules when bound to the active site of the substrate may be responsible for the cell growth inhibitory activities of the novel anthracenone and anthracene analogs.

The inhibitory effect on lipid peroxidation of these compounds were evaluated with rat brain phospholipid liposomes which provide an ideal model system for lipid peroxidation studies by Teng C. M., et. al., Eur. J. Pharmacol., vol. 303, pp. 129–139 (1996). When compared to the ascorbic acid, (+)-α-tocopherol and mitoxantrone, we found better inhibitory effect in 0.5 mM by compounds 4b and 4d (Table 2).

Furthermore, compounds 4b and 4d were significantly more efficient than ascorbic acid, (+)-α-tocopherol and mitoxantrone in 0.005 mM (Table 3).

Although not a potent inhibitor of lipid peroxidation in itself, can provide a useful template for the design of potential anticancer agents. Moreover, the results support our hypothesis that structural modification of 1,5-dichloro-9(10H)-anthracenone may lead to control of the release of active oxygen species. In fight of these finding it is suggested that cytoyoxicity activity and lipid peroxidation alone is not sufficient for potent antiproliferative action.

Whatever the molecular mechanism of the antiproliferative action of anthracenones and wherever its locus, the results described herein indicate that it is sensitive to the slightest modification in the structure of anthracenone and that active analogs can only be made if the anthracenone moiety itself is retained. In conclusion, we have presented 10-substituted 1,8dichloro-9(10H)-anthracenone derivatives which show potent inhibition of some selective cell lines. In order to understand whether or not these compounds have potent antitumor and biological activities, we will examined their effects in other tests and the results will be reported elsewhere.

All temperatures are reported in degrees centigrade. Melting points were determined with a Büchi B-545 melting point apparatus and are uncorrected. Chromatography refers to column chromatography using silica gel (E. Merck, 70–230 mesh). $^1$H-NMR spectra were recorded with a Varian GEMR-H-300 (300 MHz); δ values are in ppm relative to a tetramethylsilane internal standard. Fourier-transform IR spectra (KBr) were recorded on a Perkin-Elmer 983G spectrometer. Mass spectra (EI, 70 eV, unless otherwise stated) were obtained on a Finnigan MAT TSQ-46 and Finnigan MAT TSQ-700. UV spectra were recorded on a Shimadzu UV-160.

The compound of this invention will include various excipients; carriers or diluents and pharmaceutically approved pH of processed salts in accordance to necessity to form composition with therapeutic efficacy. Such pharmaceutical preparation could be in solid form for oral and rectum administration; liquid form or non-intestinal injection form; or ointment form for direct application on affected part. Such solid forms are manufactured according to common pharmaceutical preparation methods, which will include disintegrant like starch; sodium carboxymethyl cellulose, adhesive like ethanol; glycerine, or magnesium stearic acid; lactose to make into pharmaceutical preparation like tablets or filled into capsules or suppository. Solution or saline that include this invention compound as ingredient could use buffers of phosphoric nature to adjust the pH to suitable level, before adding adjutant; emulsifier to produce injection dose or other liquid preparation. This invention compound or pharmaceutical manufacturing could mixed synthetic acid salts with various fundamental preparations to form ointments according to known pharmaceutical manufacturing methods. Pharmaceutical compounds manufactured with this invention compound being the major ingredient could be used on mammals to produce the efficacy of this main ingredient. General dosage could be adjusted according to the degree of symptoms, and normally a person will require 50 to 300 mg each time, three times per day.

PHARMACEUTICAL ACTIVITY

Cytotoxic Activity Test. Human oral epidermoid carcinoma cells (KB cell line), human cervical carcinoma cells of ME 180 (GBM8401) and Chinese hamster ovary (CHO) cells grown in plateau phase were cultivated, and the cell proliferation assay was performed as previously described. Inhibition of cellular growth was calculated by comparison of the mean values of the test compound (N=3) with the control (N=6–8) activity: (1-test compound/control)×100.

Assay of Lipid Peroxidation. Rat brain homogenate was prepared from the brains of freshly killed Wistar rats and its peroxidation in the presence of iron ions was measured by the thiobarbituric acid (TBA) method as described. The extent of lipid peroxidation was estimated as thiobarbituric acid-reactive substances and was read at 532 nm in a spectrophotometer (Shimadzu UV-160). The results of this assay are provided in tables 2 and 3.

EXAMPLES

The following examples are representative of the practice of the invention.

Example 1

Synthesis 10-Bromo 1,5-dichloro-9(10H)-anthracenone (6)

10-Bromo 1,5-dichloro-9(10H)-anthracenone (6) to a solution of 1,5-dichloro-9(10H)-anthracenone (16.0 mmol) in $CS_2$ (30 ml) was added dropwise a solution of bromine (20.0 mmol) in $CS_2$ (5 ml). The reaction mixture was refluxed for 1 h. The reaction mixture was allowed to cool, filtered, and the filtrate was evaporated to dryness. The remaining crude product was dissolved in dichloromethane. The combined organic extracts were washed with water and dried ($MgSO_4$), and the solution was concentrated. The resulting precipitate was collected by filtration, and further purified by crystallization and chromatography to give the corresponding product.

Example 2

X-ray Crystal Structure of Compound (6)

$C_{14}H_7BrCl_2O$, Mt=342.01. A needle of the approximate dimensions 0.5×0.4×0.12 mm was mounted to glass fiber along its longest axis. The crystal system was triclinic, space group P-1. Cell constants a =7.6092(13), b=8.5639(14), and c=10.0242(14) Å; $\alpha$=76.212(11)°; $\beta$=73.058(12)°; $\gamma$=87.135(12)°; V=606.7(2) Å$^3$; Z=2; $\mu$(Mo K$\alpha$)=3.809 cm$^{-1}$; F(000)=336. Cell dimensions were determined using a Nonious CAD4 Kappa Axis XRD & Siemens Smart CCD XRD diffractometer equipped with a graphite monochromator and molybdenum source ($\gamma$=7.1073 Å). Data were collected on the same instrument using $\omega$ scans with 2$\theta$ varied from 2–50°. A total of 3090 unique reflexions were determined of which 1647 were>2.0$\sigma$. The structure was solved using direct methods and was refined using standard techniques. A total of 235 parameters were varied in the final least-squares. The refinement converged at R=0.040 and $R_w$=0.040. Residual electron density varied from 0.20 to –0.20 e/Å$^3$.

Example 3

General Procedure for the Preparation of 10-Substituted 1,5-Dichloro-9(10H)-anthracenones To a solution of compound (6) (2.0 mmol) and anhydrous calcium carbonate (0.5 g) in dry THF (20 ml) was added dropwise a solution of an appropriate alcohol or amine (3 mmol) in dry THF (10 ml) under $N_2$. The reaction mixture was stirred at room temperature or refluxed for several hours. Water (250 ml) was added and then extracted with dichloromethane. The combined organic extracts were washed with water, dried ($MgSO_4$), and concentrated. The resulting precipitate was collected by filtration, washed with water and further purified by crystallization and chromatography.

Example 4

Synthesis of 10-Propyloxy 1,5-dichloro-9(10H)-anthracenone (3c)

To a solution of compound (6) (2.0 mmol) and anhydrous calcium carbonate (0.5 g) in dry THF (20 ml) was added dropwise a solution of an appropriate propanol (10 ml) in dry THF (10 ml) under $N_2$. The reaction mixture was refluxed for 3 hours. Water (250 ml) was added and then extracted with dichloromethane. The combined organic extracts were washed with water, dried ($MgSO_4$), and concentrated. The resulting precipitate was collected by filtration, washed with water and further purified by crystallization ($CH_3CN$).

Example 5

Synthesis of 10-(iso-Butyloxy) 1,5-dichloro-9 (10H)-anthracenone (3f)

To a solution of compound (6) (2.0 mmol) and anhydrous calcium carbonate (0.5 g) in dry THF (20 ml) was added dropwise a solution of an appropriate iso-butanol (10 ml) in dry THF (10 ml) under $N_2$. The reaction mixture was refluxed for 3 hours. Water (250 ml) was added and then extracted with dichloromethane. The combined organic extracts were washed with water, dried ($MgSO_4$), and concentrated. The resulting precipitate was collected by filtration, washed with water and further purified by crystallization ($CH_3CN$).

Example 6

Synthesis of 10-(o-Toluidino) 1,5-dichloro-9(10H)-anthracenone (4c)

To a solution of compound (6) (2.0 mmol) in dry THF (20 ml) was added dropwise a solution of o-toluidine (10 ml) in dry THF (10 ml) under $N_2$. The reaction mixture was stirred at room temperature for 24 hours. Water (250 ml) was added and then extracted with dichloromethane. The combined organic extracts were washed with water, dried ($MgSO_4$), and concentrated. The resulting precipitate was collected by filtration, washed with water and further purified by crystallization ($CH_3CN$).

TABLE 1

In Vitro Cytotoxicity Activity of 10-Substituted 1,5-Dichloro-9(10 H)-anthracenones

| | | $IC_{50}$ ($\mu$M)[a] | | |
|---|---|---|---|---|
| Compound | X-R | GBM[b] | KB[c] | CHO[d] |
| 3a | $OCH_3$ | 23.5 | 8.8 | 2.9 |
| 3b | $OCH_2CH_3$ | 21.8 | 6.1 | 5.8 |
| 3c | $OCH_2CH_2CH_3$ | 11.1 | 1.8 | 42.0 |
| 3d | $OCH(CH_3)_2$ | 65.4 | 21.8 | 15.2 |
| 3e | $OCH_2CH_2CH_2CH_3$ | 29.5 | 29.5 | 8.0 |
| 3f | $OCH_2CH(CH_3)_2$ | 43.2 | 14.7 | 20.1 |
| 3g | $OCH_2C_6H_5$ | 18.5 | 93.4 | 24.7 |
| 4a | $N(CH_2CH_3)_2$ | 7.5 | 17.2 | 15.0 |
| 4b | $NH(C_6H_4)CH_3(m)$ | 11.2 | 9.5 | 6.2 |
| 4c | $NH(C_6H_4)CH_3(o)$ | 2.4 | 3.4 | 3.8 |
| 4d | $NH(C_6H_4)CH_3(p)$ | 4.6 | 11.3 | 3.0 |
| mitoxantrone-HCl | | 1.5 | 1.7 | 4.0 |

[a]The cytotoxicity tests were replicated 2 times. Each treatment has 3 replications. $IC_{50}$, drug concentration inhibiting 50% of cellular growth following 48 h of drug exposure.
[b]Human Cervical Carcinoma Cells of ME 180 (GBM8401).
[c]Human Oral Epidermoid Carcinoma Cells (KB cell line).
[d]Chinese Hamster Ovary (CHO) Cells.

TABLE 2

Inhibitory Effect of 10-Substituted 1,5-Dichloro-9(10 H)-anthracenones of the Invention on Iron-induced Lipid Peroxidation in Rat Brain Homogenates.

| Compound | X | R | Inhibition % (0.5 mM)[a] |
|---|---|---|---|
| 3a | O | $CH_3$ | 7 ± 0.1 |
| 3b | O | $CH_2CH_3$ | 7 ± 0.1 |
| 3c | O | $CH_2CH_2CH_3$ | 29 ± 2.5 |
| 3d | O | $CH(CH_3)_2$ | 13 ± 1.3 |
| 3e | O | $CH_2CH_2CH_2CH_3$ | 31 ± 3.7 |
| 3f | O | $CH_2CH(CH_3)_2$ | 38 ± 3.1 |
| 3g | O | $CH_2C_6H_5$ | 16 ± 1.5 |
| 4a | N | $(CH_2CH_3)_2$ | 12 ± 1.4 |
| 4b | NH | $(C_6H_4)CH_3(m)$ | 100 |
| 4c | NH | $(C_6H_4)CH_3(o)$ | 73 ± 3.5 |
| 4d | NH | $(C_6H_4)CH_3(p)$ | 100 |
| ascorbic acid | | | 87 ± 3.1 |
| (+)-α-tocopherol | | | 53 ± 4.4 |
| mitoxantrone-HCl | | | 64 ± 2.8 |

[a]Relative percentage of inhibition. Inhibition was compared to that of the control [ascorbic acid, (+)-α-tocopherol and mitoxantrone-HCl], $P < 0.01$, Mean ± S.E., n = 4. Values are mean percent inhibition at the indicated concentration (mM), and standard errors.

TABLE 3

Inhibitory Effects of 4b and 4d on Iron-induced Lipid Peroxidation in Rat Brain Homogenates.

| | Inhibition (%)[a] | | | |
|---|---|---|---|---|
| Compound | 5 mM | 0.5 mM | 0.05 mM | 0.005 mM |
| 4b | 100 | 100 | 92 ± 4.1 | 23 ± 2.4 |
| 4d | 100 | 100 | 94 ± 3.5 | 33 ± 2.7 |
| ascorbic acid | 100 | 87 ± 2.5 | 22 ± 2.2 | 7 ± 0.5 |
| (+)-α-tocopherol | 100 | 53 ± 1.7 | 0 | 0 |
| mitoxantrone-HCl | 100 | 64 ± 2.1 | 52 ± 3.5 | 10 ± 1.1 |

[a]Relative percentage of inhibition. Inhibition was compared to that of the control [ascorbic acid, (+)-α-tocopherol and mitoxantrone-HCl], $P < 0.01$, Mean ± S.E., n = 4. Values are mean percent inhibition at the indicated concentration (mM), and standard errors.

TABLE 4

Physicochemical data of the synthetic compounds

10-Bromo 1,5-dichloro-9(10 H)-anthracenone (6)

| | | | |
|---|---|---|---|
| yield | 95% | mp. | 201–202° C. |
| MS m/z: | 341 ($M^+$), 261 | IR (KBr) $cm^{-1}$ | 1670. |
| UV $\lambda_{max}$ ($CHCl_3$) nm (log ε) | 295 (4.57) | | |
| $^1$H-NMR($CDCl_3$) | δ: 8.11(1H, d, J = 7.1Hz), 7.65(1H, dd, J = 1.2, 8.0Hz), 7.61–7.46(4H, m), 6.62(1H, s) | | |

10-Methoxy 1,5-dichloro-9(10 H)-anthracenone (3a)

| | | | |
|---|---|---|---|
| yield | 90% | mp. | 170–171° C. |
| Anal. Calcd. For $C_{15}H_{10}O_2Cl_2$: | C, 49.15; H, 3.44 | Found: | C, 49.41; H, 3.21 |
| UV $\lambda_{max}$ ($CHCl_3$) nm (log ε) | 282 (4.72) | | |
| MS m/z: | 292 ($M^+$), 261 | IR (KBr) $cm^{-1}$ | 1670, 1068 |
| $^1$H-NMR($CDCl_3$) | δ: 8.04(1H, dd, J = 0.9, 7.6Hz), 7.63(1H, dd, J = 1.0, 7.4Hz), 7.55(1H, dd, J = 2.3, 6.6Hz), 7.52(1H, d, J = 2.5Hz), 7.51(1H, t, J = 7.3Hz), 7.45(1H, t, J = 7.8Hz), 5.76(1H, s), 3.1(3H, s). | | |

TABLE 4-continued

Physicochemical data of the synthetic compounds

| | |
|---|---|
| $^{13}$C-NMR(CDCl$_3$) | δ: 183.55, 141.99, 137.13, 135.76, 135.37, 134.94, 134.39, 133.60, 133.36, 130.65, 130.18, 129.28, 126.76, 72.52, 54.67. |
| | 10-Ethoxy 1,5-dichloro-9(10 H)-anthracenone (3b) |
| yield | 95% mp. 153–154° C. |
| Anal. Calcd. For C$_{16}$H$_{12}$O$_2$Cl$_2$: | C, 62.54; H, 3.94 Found: C, 62.18; H, 3.85 |
| UV λ$_{max}$ (CHCl$_3$) nm (log ε) | 280 (4.88) |
| MS m/z: | 306 (M$^+$), 261 IR (KBr) cm$^{-1}$ 1678, 1069 |
| $^1$H-NMR(CDCl$_3$) | δ: 8.03(1H, dd, J = 0.8, 7.6Hz), 7.61(1H, dd, 3 = 0.8, 7.6Hz), 7.54(1H, dd, J = 2.1, 6.6Hz), 7.51(1H, d, J = 5.7Hz), 7.49(1H, t, J = 7.7Hz), 7.43(1H, t, J = 7.8Hz), 5.79(1H, s), 3.32–3.25(2H, m), 1.04(3H, t, J = 6.9Hz) |
| $^{13}$C-NMR(CDCl$_3$) | δ: 183.67, 142.67, 137.06, 136.35, 135.26, 134.85, 134.31, 133.52, 133.16, 130.47, 130.07, 129.17, 126.71, 71.66, 62.87, 15.76. |
| | 10-Propyloxy 1,5-dichloro-9(10 H)-anthracenone (3c) |
| yield | 62% mp. 98–99° C. |
| Anal. Calcd. For C$_{17}$H$_{14}$O$_2$Cl$_2$: | C, 63.55; H, 4.39 Found: C, 63.28; H, 4.23 |
| UV λ$_{max}$ (CHCl$_3$) nm (log ε) | 281 (4.66) |
| MS m/z: | 320 (M$^+$), 261 IR (KBr) cm$^{-1}$ 1678, 1051 |
| $^1$H-NMR(CDCl$_3$) | δ: 8.04(1H, dd, J = 0.8, 7.6Hz), 7.62(1H, dd, J = 0.9, 7.6Hz), 7.55(1H, dd, J = 2.2, 6.5Hz), 7.52–7.48(2H, m), 7.44(1H, t, J = 7.7, 7.9Hz), 5.82(1H, s), 3.14(2H, t, J = 6.4Hz), 1.44–1.37(2H, m), 0.73(3H, t, J = 7.2, 7.4Hz). |
| $^{13}$C-NMR(CDCl$_3$) | δ: 183.65, 142.74, 137.08, 136.33, 135.22, 134.92, 134.35, 133.54, 133.14, 130.46, 130.09, 129.23, 71.60, 68.75, 23.45, 11.07 |
| | 10-(2-Propyloxy) 1,5-dichloro-9(10 H)-anthracenone (3d) |
| yield | 58% mp. 172–173° C. |
| Anal. Calcd. For C$_{17}$H$_{14}$O$_2$Cl$_2$: | C, 62.54; H, 3.94 Found: C, 62.32; H, 3.73 |
| UVλ$_{max}$ (CHCl$_3$) nm (log ε) | 287 (4.77) |
| MS m/z: | 320 (M$^+$), 261 IR (KBr) cm$^{-1}$ 1679, 1016 |
| $^1$H-NMR(CDCl$_3$) | δ: 7.99(1H, dd, J = 0.9, 7.6Hz), 7.58(1H, dd, J = 1.0, 7.6Hz), 7.50(1H, dd, J = 2.6, 7.0Hz), 7.48–7.44(2H, m), 7.41(1H, t, J = 7.8Hz), 5.83(1H, s), 3.6(1H, m), 1.06–0.88(6H, dd, J = 6.0, 6.1Hz) |
| $^{13}$C-NMR(CDCl$_3$) | δ: 84.19, 143.29, 137.43, 137.22, 134.19, 134.42, 134.06, 133.23, 133.02, 130.39, 129.05, 126.84, 69.64, 68.81, 23.61, 22.80. |
| | 10-(Butyloxy) 1,5-dichloro-9(10 H)-anthracenone (3e) |
| yield | 50% mp. 117–118° C. |
| Anal. Calcd. For C$_{18}$H$_{16}$O$_2$Cl$_2$: | C, 64.48; H, 4.81 Found: C, 64.21; H, 4.89 |
| UV λ$_{max}$ (CHCl$_3$) nm (log ε) | 280 (4.84) |
| MS m/z: | 334 (M$^+$), 261 IR (KBr) cm$^{-1}$ 1678, 1060 |
| $^1$H-NMR(CDCl$_3$) | δ: 8.04(1H, dd, J = 0.9, 7.7Hz), 7.61(1H, dd, J = 1.0, 7.7Hz), 7.55(1H, dd, J = 2.2, 6.5Hz), 7.52–7.48(2H, m), 7.44(1H, t, J = 7.8Hz), 5.81(1H, s), 3.18(2H, t, J = 6.3Hz), 1.36(2H, m), 1.17(2H, m), 0.72(3H, t, J = 7.4Hz) |
| $^{13}$C-NMR(CDCl$_3$) | δ: 183.66, 142.78, 137.12, 136.34, 135.24, 134.91, 134.33, 133.50, 133.13, 130.44, 130.13, 129.20, 126.67, 71.58, 66.63, 32.24, 19.66, 14.14 |
| | 10-(iso-Butyloxy) 1,5-dichloro-9(10 H)-anthracenone (3f) |
| yield | 65% mp. 146–147° C. |
| Anal. Calcd. For C$_{18}$H$_{16}$O$_2$Cl$_2$: | C, 64.48; H, 4.81 Found: C, 64.23; H, 4.75 |
| UV λ$_{max}$ (CHCl$_3$) nm (log ε) | 281 (4.55) |
| MS m/z: | 334 (M$^+$), 261 IR (KBr) cm$^{-1}$ 1681, 1056 |
| $^1$H-NMR(CDCl$_3$) | δ: 8.04(1H, dd, J = 0.8, 7.9Hz), 7.62(1H, dd, J = 0.9, 7.6Hz), 7.55(1H, dd, J = 2.4, 6.3Hz), 7.53(1H, d, J = 6.1Hz), 7.50(1H, t, J = 6.5Hz), 7.44(1H, t, J = 7.8Hz), 5.83(1H, s), 2.92–2.87(2H, m), |

TABLE 4-continued

Physicochemical data of the synthetic compounds

| | | | |
|---|---|---|---|
| | 1.66–1.54(1H, m), 0.70(6H, t, J = 6.8, 6.7Hz) | | |
| $^{13}$C NMR (CDCl$_3$) | δ: 183.62, 142.78, 137.07, 136.29, 135.18, 134.95, 134.36, 133.54, 133.11, 130.43, 130.09, 129.26, 126.61, 73.50, 71.52, 29.03, 19.84, 19.79 | | |

10-Benzyloxy 1,5-dichloro-9(10 H)-anthracenone (3g)

| | | | |
|---|---|---|---|
| yield | 75% | mp. | 150–151° C. |
| Anal. Calcd. For C$_{21}$H$_{14}$O$_2$Cl$_2$: | C, 68.29; H, 3.82 | Found: | C, 68.18; H, 3.68 |
| UV λ$_{max}$ (CHCl$_3$) nm (log ε) | 280 (4.83) | | |
| MS m/z: | 368 (M$^+$), 261 | IR (KBr) cm$^{-1}$ | 1676, 1047 |
| $^1$H-NMR(CDCl$_3$) | δ: 8.05(1H, d, J = 7.6Hz), 7.62(1H, d, J = 8.0Hz), 7.57(1H, d, J = 6.9Hz), 7.55–7.51(2H, m), 7.45(1H, t, J = 7.8Hz), 7.23–7.14(5H, m), 5.96(1H, s), 4.27(2H, dd, J = 6.5, 10.9Hz) | | |
| $^{13}$C-NMR (CDCl$_3$) | δ: 183.56, 142.32, 137.96, 137.21, 136.09, 135.41, 134.91, 134.43, 133.64, 133.38, 130.69, 130.20, 129.38, 128.85, 128.43, 128.34, 126.83, 71.57, 69.29 | | |

10-Diethylamino 1,5-dichloro-9(10 H)-anthracenone (4a)

| | | | |
|---|---|---|---|
| yield | 64% | mp. | 192–193° C. |
| Anal. Calcd. For C$_{16}$H$_{17}$NOCl$_2$: | 64.67; H, 5.12 | Found: | C, 64.48; H, 5.35 |
| UV λ$_{max}$ (CHCl$_3$) nm (log ε) | 275 (4.97 | | |
| MS m/z: | 333 (M$^+$), 261 | IR (KBr) cm$^{-1}$ | 1674, 1299 |
| $^1$H-NMR(CDCl$_3$) | δ: 8.07(1H, dd, J = 1.9, 7.7Hz), 7.59(1H, dd, J = 1.0, 7.8Hz), 7.47–7.31(4H, m), 5.31(1H, s), 2.59–2.20(4H, m), 0.92(6H, t, J = 7.0Hz) | | |
| | δ: 184.67, 142.83, 138.91, 138.00, 134.96, 134.25, 132.71, 131.96, 130.79, 129.30, 128.56, 125.91 58.04, 44.06, 14.13 | | |

10-(m-Toluidino) 1,5-dichloro-9(10 H)-anthracenone (4b)

| | | | |
|---|---|---|---|
| yield | 66% | mp. | 186–188° C. |
| Anal. Calcd. For C$_{21}$H$_{15}$NOCl$_2$: | C, 68.48; H, 4.10 | Found: | C, 68.27; H, 4.35 |
| UV λ$_{max}$ (CHCl$_3$) nm (log ε) | 272 (5.17) | | |
| MS m/z: | 367 (M$^+$), 261 | IR (KBr) cm$^{-1}$ | 3359, 1664 |
| $^1$H-NMR(CDCl$_3$) | δ: 8.08(1H, dd, J = 1.0, 7.7Hz), 7.65(1H, dd, J = 1.2, 7.8Hz), 7.50–7.33(4H, m), 7.07(1H, t, J = 7.8Hz), 6.61(1H, s), 6.63(1H, s), 6.56(1H, s), 6.05(1H, s), 3.72(1H, s), 2.26(3H, s). | | |
| $^{13}$C-NMR(CDCl$_3$) | δ: 183.56, 146.28, 145.88, 139.73, 138.20, 136.22, 135.35, 134.71, 134.55, 133.92, 132.50, 129.87, 129.76, 128.41, 127.54, 126.85, 121.14, 117.38, 113.30, 52.63, 22.12. MS m/z: | | |

10-(o-Toluidino) 1,5-dichloro-9(10 H)-anthracenone (4c)

| | | | |
|---|---|---|---|
| yield | 58% | mp. | 193–195° C. |
| Anal. Calcd. For C$_{21}$H$_{15}$NOCl$_2$: | C, 68.48; H, 4.10 | Found: | C, 68.19; H, 4.26 |
| UV λ$_{max}$ (CHCl$_3$) nm (log ε) | 276 (5.24) | | |
| MS m/z: | 367(M$^+$), 261 | IR (KBr) cm$^{-1}$ | 3402, 1658 |
| $^1$H-NMR(CDCl$_3$) | δ: 8.12(1H, dd, J = 0.8, 8.4Hz), 7.66(1H, dd, J = 1.3, 7.9Hz), 7.50–7.26(4H, m), 7.16(1H, d, J = 4.1Hz), 7.01(1H, d, J =7.4Hz), 6.77–6.72(2H, m), 6.08(1H, s), 3.68(1H, s), 1.87(3H, s). | | |
| $^{13}$C-NMR(CDCl$_3$) | δ: 183.56, 146.02, 144.37, 138.31, 136.31, 135.39, 134.79, 134.63, 133.89, 132.52, 131.30, 129.96, 127.62, 127.34, 126.94, 125.21, 119.97, 114.76, 114.72, 52.89, 17.98 | | |

10-(p-Toluidino) 1,5-dichloro-9(10 H)-anthracenone (4d)

| | | | |
|---|---|---|---|
| yield | 73% | mp. | 189–191° C. |
| Anal. Calcd. For C$_{21}$H$_{15}$NOCl$_2$: | C, 68.48; H, 4.10 | Found: | C, 68.56; H, 4.23. |
| UV λ$_{max}$ (CHCl$_3$) nm | 275 (5.09) | | |

TABLE 4-continued

Physicochemical data of the synthetic compounds (log ε)
MS m/z: 367(M⁺), 261    IR (KBr) cm⁻¹    3381, 1658
¹H-NMR(CDCl₃)    δ: 8.06(1H, dd, J = 1.0, 7.8Hz), 7.65(1H, dd, J = 1.2, 7.9Hz),
7.46–7.40(3H, m), 7.35(1H, t, J = 7.2Hz),
6.97(2H, d, J = 8.0Hz), 6.65(2H, d, J = 8.3Hz),
5.97(1H, s), 3.69(1H, s),
2.23(3H, s).
¹³C-NMR(CDCl₃)    δ: 183.54, 145.79, 143.76, 138.25, 136.24, 135.33,
134.69, 134.47, 133.82, 132.46, 130.43, 129.92,
129.84, 128.47, 127.66, 126.85, 117.24, 53.44,
21.07.

While there is shown and described the present preferred embodiment of the invention, it is to be distinctly understood that this invention is not limited thereto but may be variously embodied to practice within the scope of the following claims. From the foregoing description, it will be apparent that various changes may be made without departing from the spirit and scope of the invention as defined by the following claims.

What is claimed is:

1. A compound of formula 3 having a substituent $R_1$ and a substituent $R_2$:

wherein $R_1$ is selected from the group consisting of: a NH group and nitrogen;

wherein $R_2$ represents a branched or straight chain alkyl group having from 1 to 4 carbon atoms, said alkyl group being substituted with at least one substituent selected from the group consisting of a carboxyl, substituted phenyl, benzyl and substituted benzyl groups or a substituted phenyl group formula 3

2. A composition comprising a pharmaceutical compound according to claim 1 which has therapeutic utility with respect to tumor conditions; wherein the composition has the ability to inhibit the growth of human oral epidermoid carcinoma cells (KB cell line), human cervical carcinoma cells of ME 180 (GBM 8401) and Chinese hamster ovary cells (CHO) and using the formula 3 compound as the main component and various diluents and/or excipients.

3. A pharmaceutical compound which has therapeutic utility with respect to tumor conditions or antioxidant activity, and using formula 3 as the main component, various diluents and excipients could be included when necessary:

wherein $R_1$ comprises oxygen;

wherein $R_2$ represents a branched or straight chain alkyl group having from 3 to 4 carbon atoms, said alkyl group being substituted with at least one substituent selected from the group consisting of a carboxyl and substituted benzyl groups.

formula 3

4. The manufacture method for preparing 1,5-dichloro-9 (10H)-anthracenones bearing O-linked and N-linked substituents, said method comprising the steps of:

creating a reaction mixture by adding dropwise to a solution of 1,5-dichloro-9(10H)-anthracenone in $CS_2$ a solution of bromine in $CS_2$; refluxing for one hour said reaction mixture; cooling said reaction mixture; filtering said reaction mixture to create a filtrate; evaporating said filtrate to dryness to create a crude product; dissolving said crude product in dichloromethane to create a solution; washing said dichloromethane solution with water; drying said dichloromethane solution with $MgSO_4$; concentrating said dichloromethane solution; collecting the resulting precipitate by filtration; purifying by crystallization and chromatography said precipitate.

5. A compound of formula 3 having a substituent $R_1$ and a substituent $R_2$:

wherein $R_1$ is selected from the group consisting of: a NH group and nitrogen;

wherein $R_2$ represents a branched or straight chain alkyl group having from 1 to 4 carbon atoms, said alkyl group being substituted with at least one substituent selected from the group consisting of a carboxyl, substituted phenyl, benzyl and substituted benzyl groups or a substituted phenyl group;

wherein said compound has therapeutic utility with respect to tumor conditions, wherein ability to inhibit the growth of human oral epidermoid carcinoma cells (KB cell line), human cervical carcinoma cells of ME 180 (GBM 8401) and Chinese hamster ovary cells (CHO), respectively, and using formula 3 as the main component, various diluents and excipients could be included when necessary.

formula 3

6. A compound of formula 3 having a substituent $R_1$ and a substituent $R_2$:
   wherein $R_1$ is selected from the group consisting of: a NH group and nitrogen;
   wherein $R_2$ represents a branched or straight chain alkyl group having from 3 to 4 carbon atoms, said alkyl group being substituted with at least one substituent selected from the group consisting of a carboxyl, hydrogen, substituted phenyl, benzyl and substituted benzyl groups or a substituted phenyl group.

formula 3

* * * * *